United States Patent [19]

Yamamori et al.

[11] Patent Number: 5,738,106

[45] Date of Patent: Apr. 14, 1998

[54] CAPNOMETER

[75] Inventors: Shinji Yamamori; Kohei Ono; Masami Ito; Hiromitsu Kasuya; Masayuki Inoue; Masaki Sugiura, all of Tokyo, Japan

[73] Assignee: Nihon Kohden Corporation, Tokyo, Japan

[21] Appl. No.: 605,928

[22] Filed: Feb. 23, 1996

[30] Foreign Application Priority Data

Feb. 23, 1995 [JP] Japan ............... 7-034967

[51] Int. Cl.$^6$ ................... A61B 5/008
[52] U.S. Cl. ................... 128/719; 128/664
[58] Field of Search ................... 128/716, 718, 128/719, 204.22, 204.23, 633, 664; 73/23.3

[56] References Cited

U.S. PATENT DOCUMENTS

| | | | |
|---|---|---|---|
| 3,565,058 | 2/1971 | Mansfield | 128/701 |
| 4,067,320 | 1/1978 | Olsson et al. | 128/2 C |
| 4,269,194 | 5/1981 | Rayburn et al. | |
| 4,423,739 | 1/1984 | Passaro et al. | 128/719 |
| 4,653,498 | 3/1987 | New, Jr. et al. | 128/633 |
| 4,907,166 | 3/1990 | Corenman et al. | 128/719 |
| 5,081,998 | 1/1992 | Yelderman et al. | 128/719 |
| 5,095,896 | 3/1992 | Omoigui | |
| 5,095,913 | 3/1992 | Yelderman et al. | |
| 5,363,857 | 11/1994 | Howard | 128/719 |

FOREIGN PATENT DOCUMENTS

| | | |
|---|---|---|
| 0 512 535 A2 | 11/1992 | European Pat. Off. |
| 42 01 285 A1 | 7/1992 | Germany |
| 51-136474 | 11/1976 | Japan |
| 53-53184 | 5/1978 | Japan |
| 59-160446 | 9/1984 | Japan |
| 9325142 | 12/1993 | WIPO ............... 128/719 |

OTHER PUBLICATIONS

Lathi, B.P., "Modern Digital & Analog Communication Systems," The Dryden Press, Saunders College Publishing, Philadelphia, 1989, pp. 6 & 7.

*Primary Examiner*—Jennifer Bahr
*Assistant Examiner*—Bryan K. Yarnell
*Attorney, Agent, or Firm*—Sughrue, Mion, Zinn, Macpeak & Seas, PLLC

[57] ABSTRACT

The capnometer of the invention is an equipment which detects a signal which time-varies in accordance with a carbon dioxide concentration from a respiration gas, thereby calculating the carbon dioxide concentration. The capnometer has: carbon dioxide concentration calculating device for detecting the maximum value for each expiration from a concentration signal corresponding to the calculated carbon dioxide concentration, for comparing the maximum value with concentration signals respectively corresponding to a plurality of predetermined concentration ranges, and for outputting one of different control signals for the concentration ranges; and reporting device for outputting a sound corresponding to the carbon dioxide concentration, in accordance with the control signal.

8 Claims, 6 Drawing Sheets

1ST BEEPER    2ND BEEPER    3RD BEEPER    4TH BEEPER

THREE INTERMITTENT SOUND    TWO INTERMITTENT SOUND    SINGLE SOUND

FIG. 6

FIG. 7A
1ST BEEPER
3KHz

200ms

FIG. 7B
2ND BEEPER
1KHz

200ms

FIG. 7C
3RD BEEPER
750KHz

200ms

FIG. 7D
4TH BEEPER
10KHz
INTERMITTENT SOUND

CAPNOMETER

BACKGROUND OF THE INVENTION

1. Field of the Invention

The invention relates to a capnometer which, when carbon dioxide is to be measured, outputs a sound corresponding to the carbon dioxide concentration.

2. Related Art

In a medical first aid site such as a traffic accident, generally, a capnometer which measures the carbon dioxide concentration of expiration of a patient to be first-aided is used as means for checking that the airway of the patient is open. In consideration of a power source, it is required at a medical first aid site to use a portable equipment powered by a battery. A prior art capnometer comprises a bar-graph indicator which uses light emitting devices such as LEDs, as concentration indicating means, and is configured in such a manner that the length of the bar varies depending on the carbon dioxide concentration in the expiration of the patient. Numerals indicating a scale of the carbon dioxide concentration are printed in the side portion of the bar-graph indicator so that the carbon dioxide concentration in the expiration can be read.

However, accidents which should be urgently treated happen in all times and place. When the capnometer is used in the daytime or while it is light, the display of the bar graph is difficult to read, and, when it is used in the nighttime, a bar graph is clearly displayed but the numerals indicating a scale cannot be read, thereby producing a problem in that the display using only such a bar-graph display is insufficient for correctly knowing the carbon dioxide concentration in the expiration of a patient.

SUMMARY OF THE INVENTION

In view of the above problem, therefore, it is an object of the invention to provide a capnometer which can output a sound corresponding to a carbon dioxide concentration.

The capnometer of the present invention is an equipment which detects a signal which varies in accordance with a carbon dioxide concentration in a respiration gas. The capnometer comprises: carbon dioxide concentration calculating means for detecting a concentration signal corresponding to a carbon dioxide concentration for each respiration, for comparing the concentration signal with concentrations respectively corresponding to a plurality of predetermined concentration ranges, and for outputting one of different control signals for the concentration ranges; and beeper means for outputting a sound corresponding to the carbon dioxide concentration, in accordance with the control signal.

According to the present invention, the beeper means outputs an intermittent sound for each respiration in response to the control signal, the intermittent sound having one number of delay intervals from among a plurality of different numbers of delay intervals which are predetermined in accordance with the concentration ranges.

According to the present invention, the beeper means comprises means for converting a level of the concentration signal into a frequency corresponding to the level, and the beeper means outputs a sound for each respiration in response to the control signal, the sound having one of frequencies which are predetermined in accordance with the concentration ranges.

According to the present invention, the beeper means comprises means for converting a level of the concentration signal into a frequency corresponding to the level, and outputs a sound for each respiration, the sound having frequencies which correspond to the change of the carbon dioxide concentration.

In the present invention, the carbon dioxide concentration calculating means detects the maximum value for each expiration from a concentration signal corresponding to a carbon dioxide concentration for each expiration, compares the value with concentrations respectively corresponding to a plurality of predetermined concentration ranges, and outputs one of different control signals for the concentration ranges, and the beeper means outputs a sound in accordance with the control signal.

In the present invention, the beeper means outputs an intermittent sound for each respiration in response to the control signal, the intermittent sound having one of different interruption numbers which are predetermined in accordance with the concentration ranges.

In the present invention, the beeper means is provided with means for converting a level of the concentration signal into a frequency corresponding to the level, and the beeper means outputs a sound for each respiration in response to the control signal, the sound having one of frequencies which are predetermined in accordance with the concentration ranges.

In the present invention, the beeper means is provided with means for converting a level of the concentration signal into a frequency corresponding to the level, and outputs a sound for each respiration, the sound corresponding to the change of the carbon dioxide concentration.

DETAILED DESCRIPTION OF THE PREFERRED EMBODIEMTNS

Figure 1:
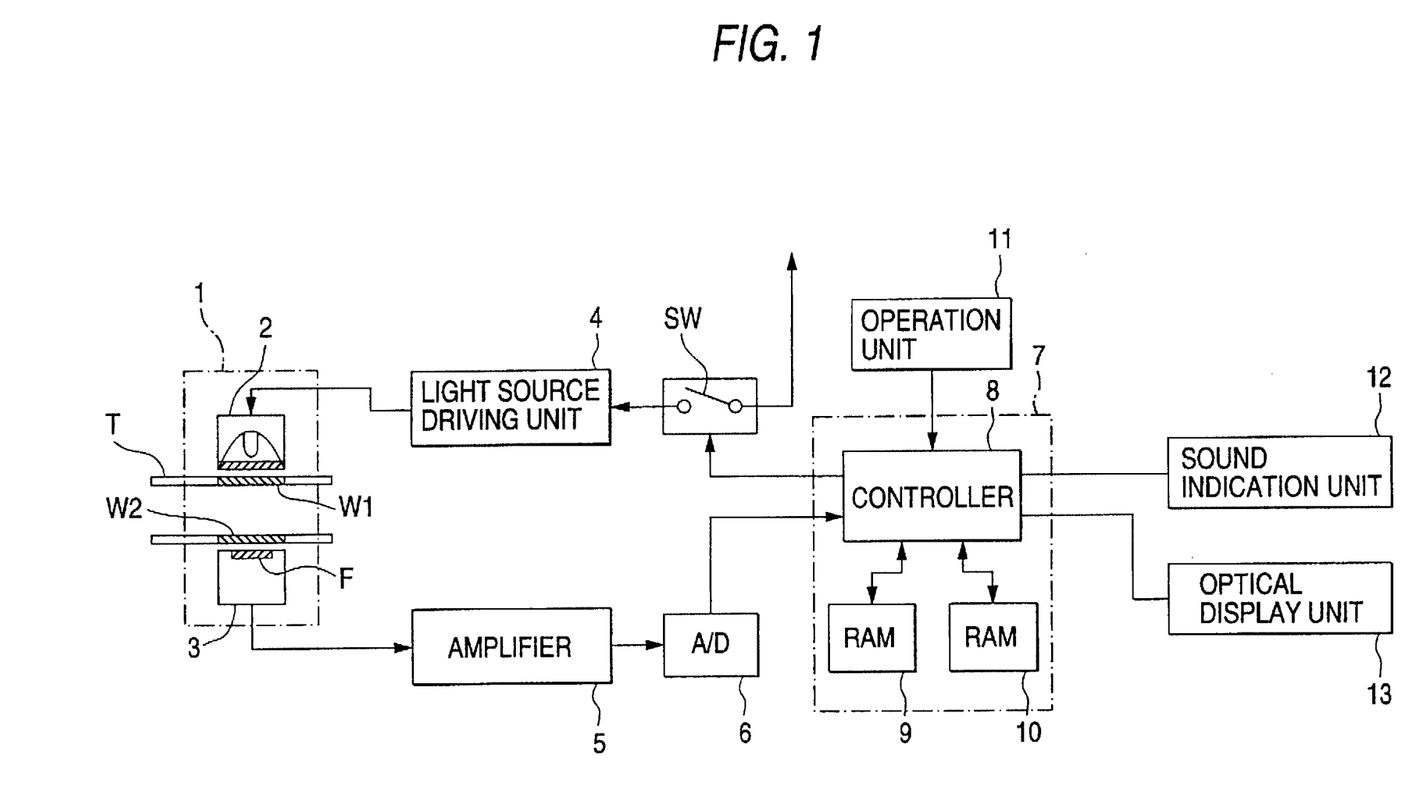
FIGS. 1 and 2 are block diagrams showing the configuration of the capnometer of the invention.
Figure 2:
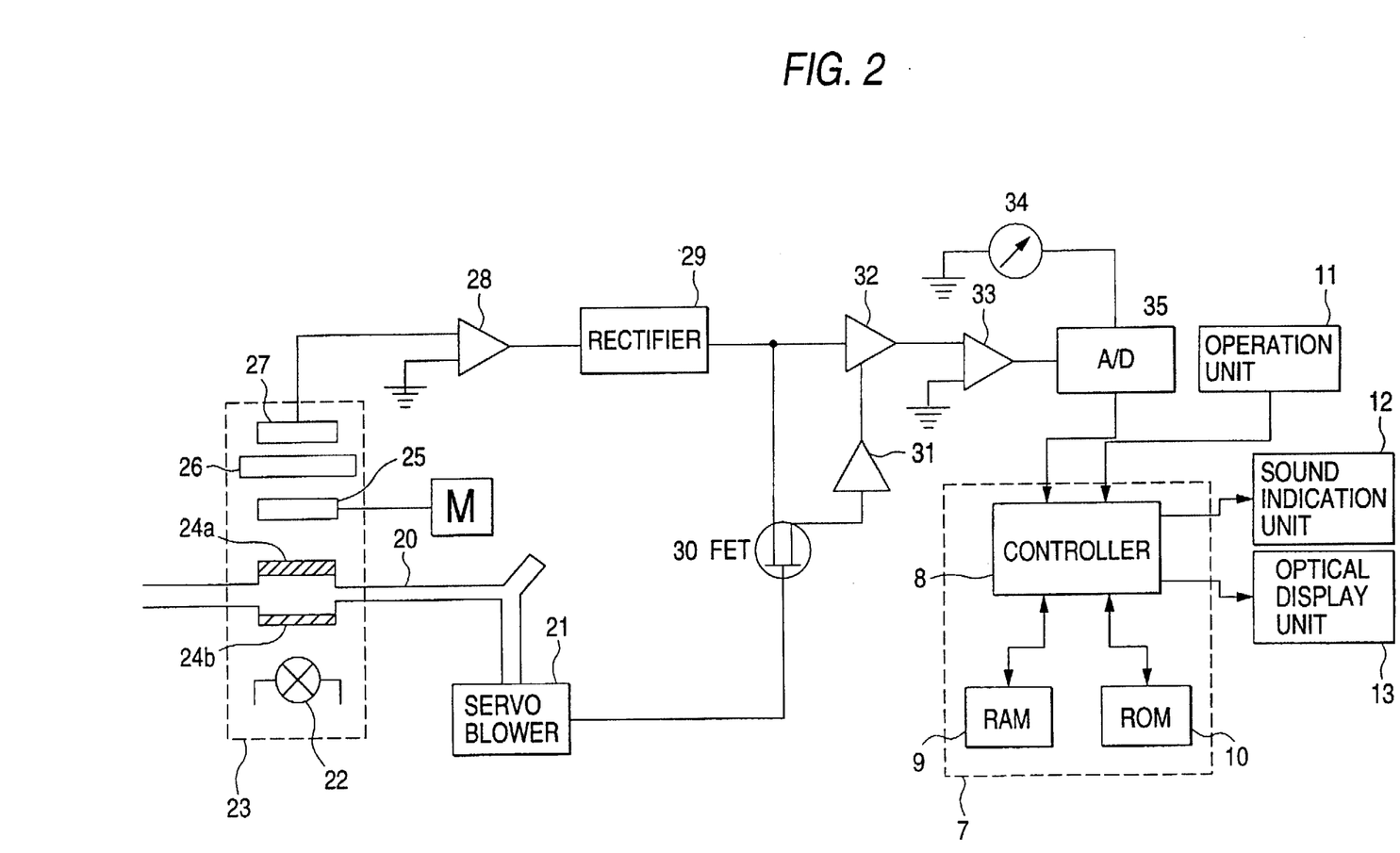
Figure 3:
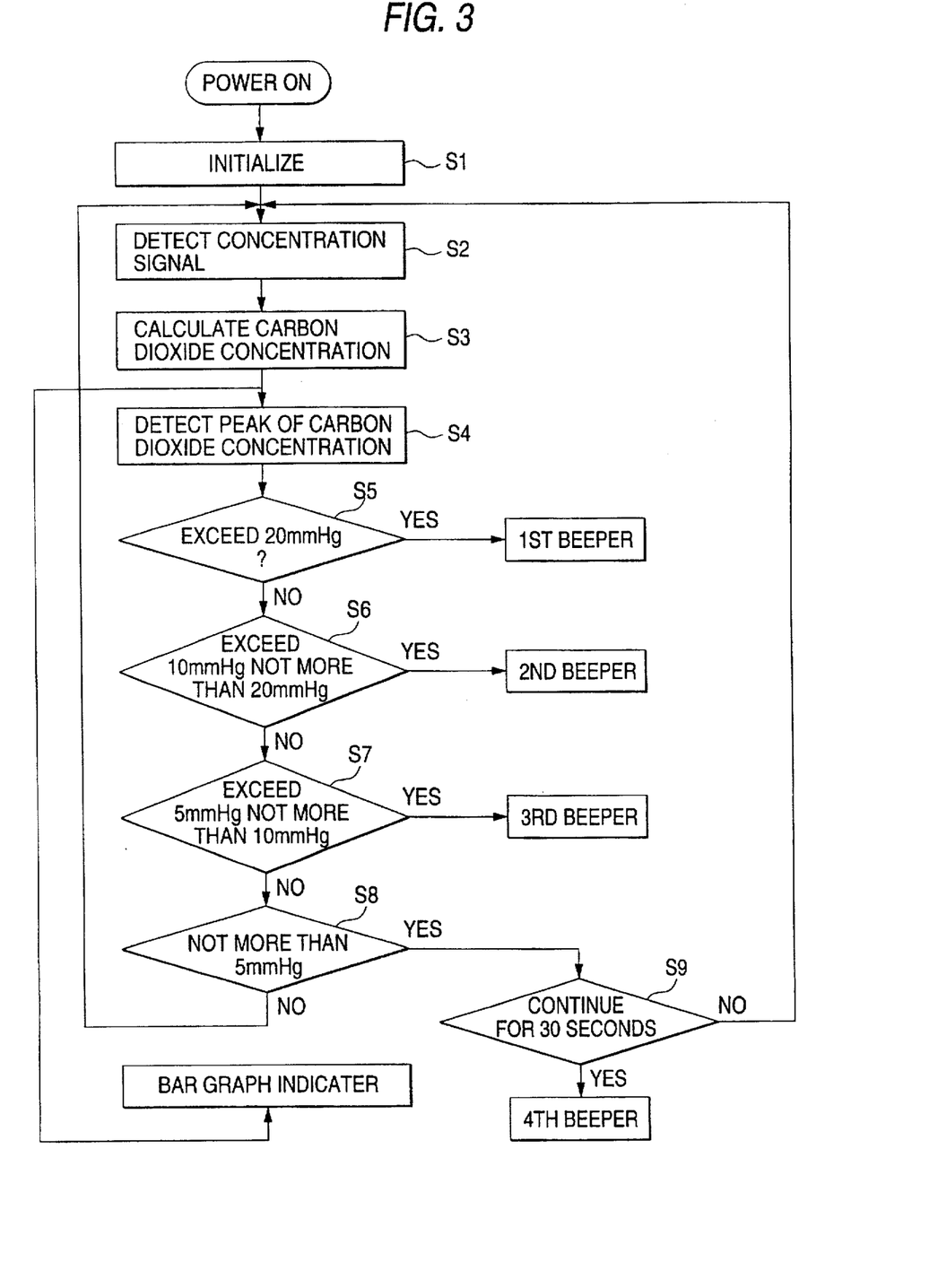
FIG. 3 is a flowchart illustrating the report procedure of the embodiment of FIG. 1.
Figure 4:
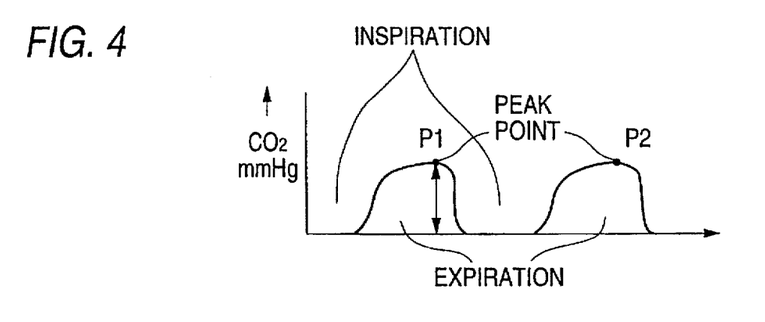
FIG. 4 is a waveform chart of a carbon dioxide concentration and illustrating a peak detected in the embodiment of FIG. 1.
Figure 8:
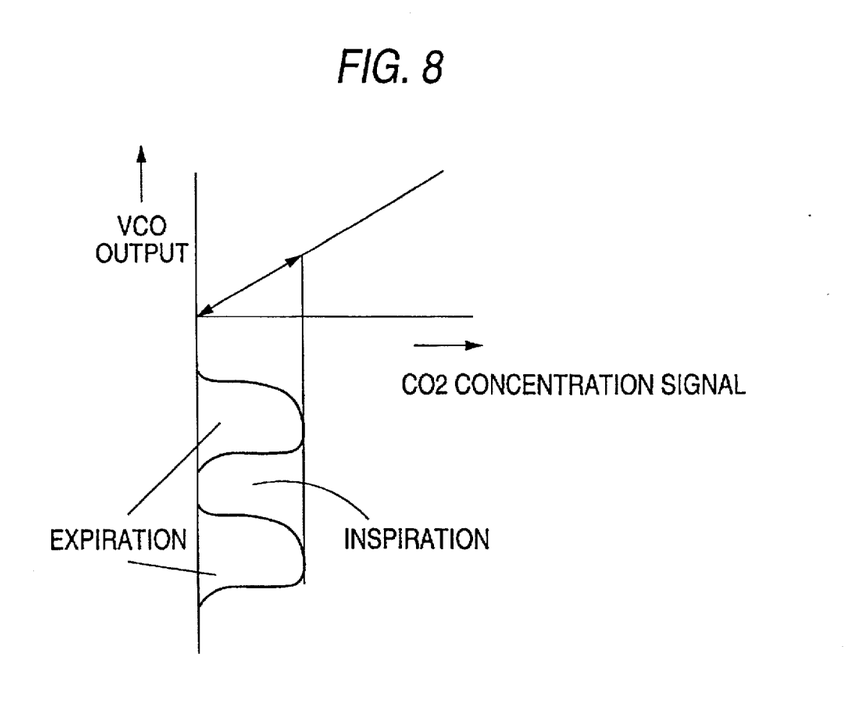
FIG. 8 is a diagram showing another report example in the other embodiment of FIG. 6.
Figure 9:
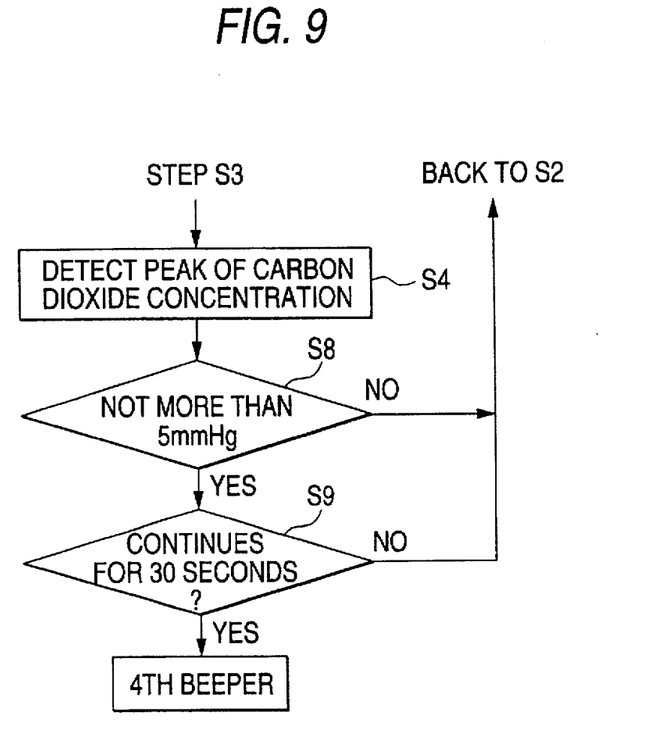
FIG. 9 is a flowchart showing the procedure in detection of apnea in the report example of FIG. 8.

Hereinafter, embodiments of the capnometer of the invention will be described with reference to the accompanying drawings. FIGS. 1 and 2 are block diagrams showing the configuration of embodiments of the invention, FIG. 3 is a flowchart showing the procedure of the embodiment of FIG. 1, FIG. 4 is a waveform chart of a carbon dioxide concentration and showing a peak detected for each expiration, FIG. 5 shows four report examples in the embodiment of FIG. 1, FIG. 6 is a schematic block diagram showing the main portions of another embodiment of FIG. 1, FIG. 7 shows four report examples in another embodiment of FIG. 6, FIG. 8 shows another report example in the other embodiment of FIG. 6, and FIG. 9 is a flowchart showing the procedure in detection of apnea in the report example of FIG. 8.

In FIG. 1, 1 designates a concentration signal detection unit comprising a light source 2 emitting infrared radiation, an airway adapter T, and an infrared sensor 3 which consists of, for example, a thermopile and opposes the light source 2 via the airway adapter T. A filter F for a wavelength (about 4.3 µm) which can be absorbed by carbon dioxide in an expiration gas is disposed on the light sensing area of the infrared sensor 3. In the airway adapter T, windows W1 and W2 which are made of an optically transparent material such as a plastic sheet and subjected to an antifogging process are formed at portions which correspond to the light source 2 and the infrared sensor 3, respectively, so that infrared rays from the light source 2 reach the infrared sensor 3. One end (the left end in the figure) of the airway adapter T serves as an insertion end which is to be inserted into the mouth of a patient, and the other end (the right end in the figure) serves as an end which is opened in the air. The other end may be connected to a bag or a ventilator.

The reference numeral 4 designates a light source driving unit which consists of, for example, a constant-current circuit and is turned on/off by a switch SW. The switch SW consists of a semiconductor switch such as a transistor and is turned on/off at a predetermined period by a control signal output from a controller 8 which will be described later. When the infrared sensor 3 is configured by a thermopile, the switch SW is disposed in order to compensate a drift of the output voltage and a change in sensitivity which are caused by variation in ambient temperature or fogging of the windows W1 and W2, and turned on/off, for example, for each respiration (inspiration and expiration) or every one minute.

The reference numeral 5 designates an amplifier which amplifies the detection voltage of the infrared sensor 3, and 6 designates an analog/digital converter which converts the output of the amplifier 5 into a digital signal.

The reference numeral 7 designates a carbon dioxide concentration calculation unit which comprises the controller 8 consisting of a CPU, a RAM 9, and a ROM 10. In accordance with a control program previously stored in the ROM 10, the calculation unit compensates the drift of the output voltage and the sensitivity of the infrared sensor 3, calculates the carbon dioxide concentration, and detects the peak value of a concentration signal corresponding to the calculated carbon dioxide concentration. The RAM 9 temporarily stores preset data, process data, etc. The carbon dioxide concentration calculation unit 7 sends the control signal to a sound indicator 12 which will be described later, on the basis of a result of a comparison of the calculated carbon dioxide concentration and a plurality of carbon dioxide concentration ranges previously set in the control program of the ROM 10.

The reference numeral 11 designates an operation unit which consists of, for example, a plurality of buttons and through which parameters such as the on/off period of the light source 2, required data, and the like are set.

The reference numeral 12 designates the sound indicator which consists of a sound device such as a buzzer or a loudspeaker and which is caused to output a sound for each respiration by the control signal output from the carbon dioxide concentration calculation unit 7 and corresponding to the carbon dioxide concentration.

The reference numeral 13 designates an optical display unit in which, for example, a plurality of LEDs (light emitting diodes) are linearly arranged so as to display a bar graph and numerals respectively corresponding to carbon dioxide concentrations are attached to a side portion by printing or the like. A known display unit may be used as the optical display unit 13 which conducts the bar-graph display.

FIG. 2 shows the configuration of a capnometer which is another embodiment and comprises a drift compensation device. In FIG. 2, 20 designates a connection tube through which a respiration gas passes. One end of the connection tube is a connection end which is to be held in the mouth of the subject, and the other end is branched into two parts one of which is opened and the other of which is connected to a servo ventilator 21 for supplying air to the patient in inspiration. A pair of optically transparent windows 24a and 24b which are made of glass or the like are formed at the intermediate portion of the connection tube 20. A light source 22 is disposed below the window 24b, and a radiation interrupter 25 having an optical through hole and rotated by a motor M is disposed above the window 24a. A filter 26 which passes only light of a wavelength which can be absorbed by carbon dioxide is disposed above the optical interrupter 25. An optical detector 27 is disposed above the filter 26. The reference numeral 28 is an amplifier which amplifies the output voltage of the optical detector 27, and 29 designates a rectifier. The reference numeral 32 designates a divider, 33 designates a logarithmic amplifier, and 34 designates a recorder. The reference numeral 30 designates an FET (field effect transistor) which is turned on during each inspiration period by the output of the servo ventilator 21, and 31 designates a memory which holds the voltage corresponding to carbon dioxide concentration of "0" during an inspiration period, and outputs the voltage to the divider 32.

In this configuration, light emitted from the light source 22 passes through the window 24a and a respiration gas in the connection tube 20, and then enters the optical detector 27 via the window 24a and the filter 26 in the form of light interrupted by the optical interrupter 25. The optical detector 27 detects the amount of light which corresponds to the carbon dioxide concentration. The output signal is amplified by the amplifier 28 and then rectified by the rectifier 29.

The output of the optical detector 27 contains a change in amount of light due to contamination of the filter 26 and the windows 24a and 24b, and a drift such as variation in light intensity of the light source 22. In order to remove a drift component from the output voltage of the rectifier 29, therefore, the servo ventilator 21 outputs a positive voltage during an inspiration period to the FET 30 so that the FET is turned on. As a result, the voltage corresponding to carbon dioxide concentration of "0" is held by the memory 31 and output to the divider 32. When an inspiration period is ended, the servo ventilator 21 ceases from outputting the positive voltage, with the result that the FET 30 is turned off and the output (the signal corresponding to carbon dioxide in the expiration) is supplied to the divider 32. The output is divided by the voltage corresponding to carbon dioxide concentration of "0" which is held by the memory 31, so that the drift component is eliminated from the output, thereby calibrating the zero point. The output of the divider 32 is supplied to the logarithmic amplifier 33 to obtain an output signal which is proportional to the carbon dioxide concentration.

The obtained output signal is sent to the carbon dioxide concentration calculation unit 7. Thereafter, the signal and report processes may be conducted in the same manner as those of the embodiment of FIG. 1.

The beeper process in the above-described configuration will be described with reference to the flowchart of FIG. 3 and the beeper examples shown in FIG. 5. At first, the power source is turned on and the equipment is initialized (step S1).

In the concentration signal detection unit 1, infrared rays from the light source 2 are passed through a respiration gas passing through the airway adapter T, and the infrared sensor 3 detects light corresponding to the concentration of carbon dioxide contained in the gas and outputs the concentration signal (step S2). The concentration signal is sent to the carbon dioxide concentration calculation unit 7 via the amplifier 5 and the analog/digital converter 6 and the carbon dioxide concentration is calculated (step S3).

Then, the peak of the carbon dioxide concentration is detected for each expiration (step S4). In this case, as shown in FIG. 4, peaks P1 and P2 are respectively detected for expirations from the calculated carbon dioxide concentration, by the controller 8.

Figure 5A:
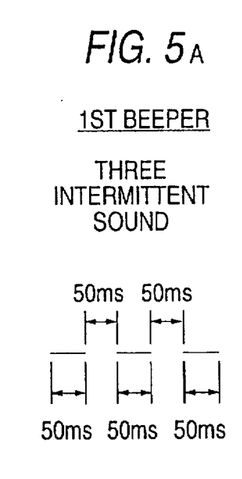
FIG. 5 is a diagram showing report examples in the embodiment of FIG. 1.
Figure 6:
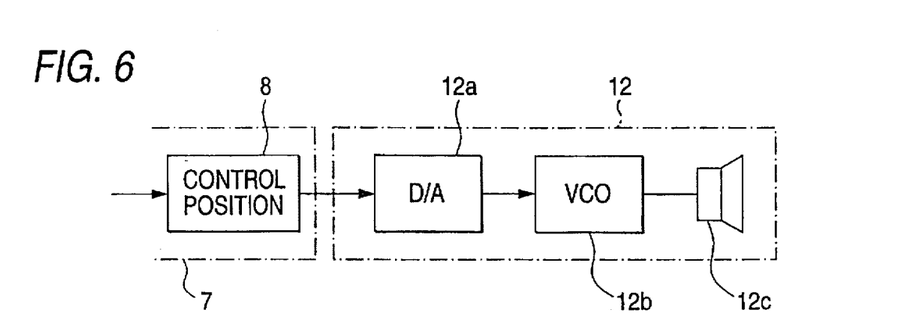
FIG. 6 is a block diagram showing the main portions of another embodiment.

When the carbon dioxide concentration exceeds 20 mmHg (step S5), the controller 8 outputs a control signal for the 1st beeper to the sound indication unit 12 so that an intermittent sound shown in FIG. 5A is produced. In the 1st beeper, for example, an intermittent sound consisting of three continuation periods and two intervals is produced for each respiration. Each of the periods and intervals continues for 50 ms.

Figure 5B:
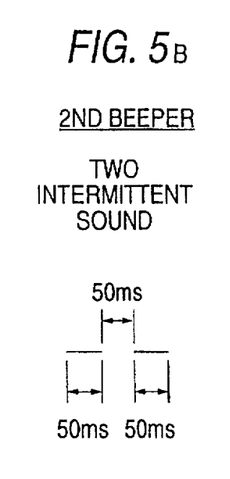

When the carbon dioxide concentration exceeds 10 mmHg and is not greater than 20 mmHg (step S6), the controller 8 outputs a control signal for the 2nd beeper to the sound indicator unit 12 so that an intermittent sound shown in FIG. 5B is produced. In the 2nd beeper, for example, an intermittent sound consisting of two continuation periods and one interval is produced for each respiration. Each of the periods and intervals continues for 50 ms.

Figure 5C:
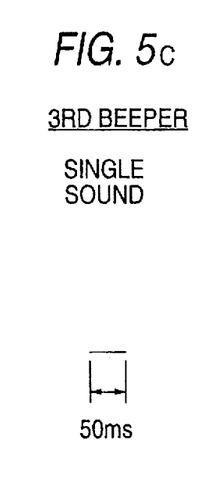

When the carbon dioxide concentration exceeds 5 mmHg and is not greater than 10 mmHg (step S7), the controller 8 outputs a control signal for report 3 to the sound indicator unit 12 so that a sound shown in FIG. 5C is produced. In the 3rd beeper, for example, a single sound continuing for 50 ms is produced for each expiration.

If it is judged in each of the concentration judgments of steps S5 to S7 that the concentration is not in the respective ranges, the process proceeds to the succeeding step.

Figure 5D:
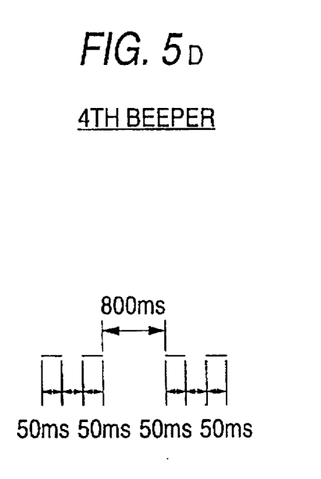

When the carbon dioxide concentration is not greater than 5 mmHg or a dangerous condition occurs (step S8), it is judged whether the duration of the condition exceeds 30 seconds or not (step S9). If the condition continues for 30 seconds or longer, it is judged that the patient is in an apnea state, and the controller 8 outputs a control signal for the 4th beeper to the sound indicator 12 so that a sound shown in FIG. 5D is produced. In the 4th beeper, two sounds each of which consists of two continuation periods of 50 ms and one interval of 50 ms are produced at an interval of 800 ms, thereby warning the emergency condition.

If it is judged in step S8 that the carbon dioxide concentration is greater than 5 mmHg, the process returns to step S2 and the above procedure is repeated. If the duration of the condition in which the carbon dioxide concentration is 5 mmHg or less is shorter than 30 seconds, the process returns to step S2 and the above procedure is repeated.

The carbon dioxide concentration data which is calculated in step S3 is supplied to the optical display unit 13 and, in the same manner as the prior art, the carbon dioxide concentration in respiration is always displayed in the form of a bar graph which expands or contracts in accordance with the concentration.

In this example, therefore, the number of delay intervals of the intermittent sound in respiration is changed in accordance with the change of the carbon dioxide concentration, thereby enabling the carbon dioxide concentration to be judged.

FIG. 6 is a schematic diagram showing the main portions of another embodiment. The portions corresponding to those of the embodiment of FIG. 1 are designated by the same reference numerals. Also the carbon dioxide concentration calculation unit 33 and the display units 38 and 39 in the embodiment of FIG. 2 can operate in the same manner. In FIG. 6, the sound indicator 12 comprises a digital/analog converter 12a, a voltage controlled oscillator (VCO) 12b which converts the concentration signal into a frequency, and a sound device 12c which outputs a sound and consists of, for example, a buzzer or a small loudspeaker.

In this configuration, the controller 8 outputs a concentration signal corresponding to the carbon dioxide concentration. The concentration signal is converted into an analog signal by the digital/analog converter 12a, and the analog concentration signal is sent to the VCO 12b which in turn converts the concentration signal into a frequency and outputs it to the sound device 12c. The sound device 12c produces a sound of the frequency which corresponds to the concentration signal. For example, a sound of a high frequency is produced when the carbon dioxide concentration is high, and a sound of a low frequency is produced when the carbon dioxide concentration is low. The processes of judging the carbon dioxide concentration are the same as steps S5 to S9 in the above-described flowchart of FIG. 3 and hence their description is omitted.

Figure 7A:
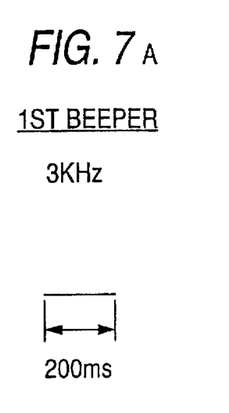
FIG. 7 is a diagram showing report examples in the other embodiment of FIG. 6.
Figure 7B:
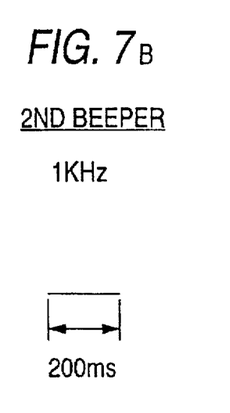
Figures 7C, 7D:
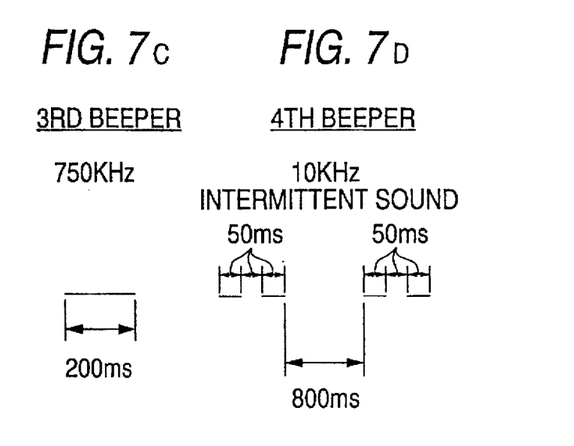

FIG. 7 shows four examples of the sound produced by the sound device 12c (FIG. 6). When the carbon dioxide concentration exceeds 20 mmHg, 1st beeper is conducted so that a single sound of, for example, 3 kHz is produced for 200 ms for each respiration (FIG. 7A). When the carbon dioxide concentration exceeds 10 mmHg and is not greater than 20 mmHg, 2nd beeper is conducted so that a single sound of, for example, 1 kHz is produced for 200 ms (FIG. 7B). When the carbon dioxide concentration exceeds 5 mmHg and is not greater than 10 mmHg, 3rd beeper is conducted so that a single sound of, for example, 750 Hz is produced for 200 ms (FIG. 7C). When the carbon dioxide concentration is not greater than 5 mmHg and this condition continues for 30 seconds or longer, it is judged that the patient is in an apnea state, and two intermittent sounds of, for example, 10 kHz and each having an interval of 50 ms are produced at an interval of 800 ms (FIG. 7D). In this way, when the carbon dioxide concentration in expiration of the patient is lowered, a sound of a low frequency is produced, and, in an apnea state of higher emergency, the number of producing sounds is made different so that the state can be rapidly known. Consequently, the state of the carbon dioxide concentration can be easily judged from the pitch of a sound.

FIG. 8 shows another beeper example in a second embodiment of FIG. 6. In this example, one of sounds of different frequencies is continuously produced in accordance with the carbon dioxide concentration which changes in expiration. As the carbon dioxide concentration in expiration is higher, a continuous sound of a higher frequency is produced. When the carbon dioxide concentration is lowered, the operation is conducted in the reversed manner.

FIG. 9 is a flowchart showing the procedure of the 4th beeper in a third embodiment of FIG. 6. In this case, the process proceeds from step S4 of detecting the peak value of the carbon dioxide concentration in the flowchart of FIG. 3, to step S8 in which it is judged whether the carbon dioxide concentration is not greater than 5 mmHg or not. The procedure is identical with that of the flowchart of FIG. 3. In the example of FIG. 9, a continuous sound is produced in accordance with the change of the carbon dioxide concentration, and hence the controller 8 of the carbon dioxide concentration calculation unit 7 does not conduct the judgment process for the 1st to 3rd beeper corresponding to steps S5 to S7.

In this example, one of sounds of different frequencies is continuously produced for each respiration in accordance with the carbon dioxide concentration, and therefore the respiration state of the patient can be easily known.

In the first and second embodiments, as shown in FIG. 4, the peak of the carbon dioxide concentration is detected for each expiration. Alternatively, the end tidal volume may be used in place of the peak value.

As described above, according to the invention set forth claims 1 to 3, ranges of the carbon dioxide concentration are previously determined, and one of sounds respectively corresponding to the ranges is produced, whereby the condition of the carbon dioxide concentration in respiration of a patient can be audible known. Therefore, the invention is effective in judgment of the carbon dioxide concentration of a patient in the nighttime or at dark place.

According to the present invention, a sound is produced for each respiration in accordance with the change of the carbon dioxide concentration, thereby providing an effect that existence of respiration can be easily known.

What is claimed is:

1. A capnometer comprising:

carbon dioxide concentration calculating means for detecting a concentration signal corresponding to a carbon dioxide concentration for each expiration, for comparing said concentration signal with concentrations respectively corresponding to a plurality of predetermined concentration ranges, and for outputting a control signal, from among different control signals respectively corresponding to said predetermined concentration ranges, corresponding to a detected carbon dioxide concentration; and beeper means for outputting a sound corresponding to the detected carbon dioxide concentration in accordance with said control signal;

wherein said beeper means outputs an intermittent sound for each respiration in response to said control signal, said intermittent sound having a predetermined number of delay intervals, each of said concentration ranges having an associated intermittent sound with a predetermined number of delay intervals.

2. The capnometer according to claim 1, wherein said beeper means comprises means for converting a level of said concentration signal into a frequency corresponding to the level, said beeper means outputting a sound for each respiration in response to said control signal, said sound having a predetermined frequency, each of said concentration ranges having an associated predetermined frequency.

3. The capnometer according to claim 1, wherein said beeper means includes means for converting a level of said concentration signal into a frequency corresponding to the level, and outputs a sound for each expiration, said sound corresponding to the change of the detected carbon dioxide concentration.

4. The capnometer according to claim 1, wherein said carbon dioxide concentration calculating means includes an infrared rays detector.

5. The capnometer according to claim 4, wherein said infrared rays detector includes a thermopile.

6. A method for calculating the carbon dioxide concentration from a respiration gas, comprising the steps of:

detecting a concentration signal corresponding to a detected carbon dioxide concentration for each expiration;

comparing said concentration signal with concentrations respectively corresponding to a plurality of predetermined concentration ranges;

outputting a control signal, from among different control signals respectively corresponding to said predetermined concentration ranges, corresponding to said detected carbon dioxide concentration; and outputting a sound corresponding to the detected carbon dioxide concentration, in accordance with said control signal;

wherein said step of outputting a sound comprises the step of outputting said sound which includes an intermittent sound for each respiration in response to said control signal, said intermittent sound having a predetermined number of delay intervals, each of said concentration ranges having an associated intermittent sound with a predetermined number of delay intervals.

7. The method according to claim 6, further comprising the steps of:

converting a level of said concentration signal into a frequency corresponding to the level;

wherein said sound for each expiration is in response to said control signal, and said sound has a predetermined frequency, each of said concentration ranges having an associated predetermined frequency.

8. The method according to claim 6, further comprising the steps of:

converting a level of said concentration signal into a frequency corresponding to the level; and outputting a sound for each expiration, said sound corresponding to the change of the detected carbon dioxide concentration.

* * * * *